United States Patent [19]

Chayen et al.

[11] Patent Number: 5,763,479
[45] Date of Patent: Jun. 9, 1998

[54] NAPHTHOQUINONE DERIVATIVES FOR THE TREATMENT OF CHRONIC INFLAMMATION

[75] Inventors: Joseph Chayen; Lucille Bitensky, both of Richmond; George T. B. Frost, Farnham, all of United Kingdom

[73] Assignee: KS Biomedix Ltd., Surrey, United Kingdom

[21] Appl. No.: 87,743

[22] PCT Filed: Feb. 3, 1992

[86] PCT No.: PCT/GB92/00196

§ 371 Date: Jul. 12, 1993

§ 102(e) Date: Jul. 12, 1993

[87] PCT Pub. No.: WO92/01353

PCT Pub. Date: Aug. 20, 1992

[30] Foreign Application Priority Data

Feb. 4, 1991 [GB] United Kingdom ............... 9102340
Nov. 19, 1991 [GB] United Kingdom ............... 9124541

[51] Int. Cl.$^6$ ................................... A01N 43/20
[52] U.S. Cl. ................. 514/475; 514/434; 514/455; 514/468; 514/641; 514/681; 514/682
[58] Field of Search .................. 514/475, 434, 514/455, 468, 641, 691, 25, 682

[56] References Cited

U.S. PATENT DOCUMENTS 2,367,302  1/1945  Moore et al. ............... 552/299
4,628,062  12/1986  Opitz et al. ............... 54/682

FOREIGN PATENT DOCUMENTS 0 147 778  7/1985  European Pat. Off. .

OTHER PUBLICATIONS

Pitsillides, A.A., et al. "The effect of menadione epoxide on the experimental immune arthritis in the rabbit", Int. J. Exp. Path., 72, pp. 301–309, 1991.

Fontagne, J. et al., "Inflammatory and anti-inflammatory properties of some oxidizing substances", Arch. Int. Pharmacodyn. Ther., 206(2), pp. 242–252, 1973.

Rabotnikov, Yu. M., "Characteristics and analysis of the antiphlogistic effect of vikasol", Sb. Nauch. Tr., 63, pp. 126–42, 1966.

Agents and Actions, vol. 12, No. 4, 1982, Birkhauser Verlag, Basel, CH; J. Chayen: "Editorial Concerning the possibiliity of redox drugs", pp. 530–535.

The Journal of Rheumatology, vol. 11, No. 5, Oct. 1984; F. Huck et al: "Reducing Property of Some Slow Acting Antirheumatic Drugs", pp. 605–609.

Pitsillides et al., "Amelioration by Menadione of the Experimental Chronic Immune Arthritis in the Rabbit", Cell Biochemistry and Function, vol. 8, (1990).

Chayen et al., "The Use of Menadione as an Intermediate Hydrogen–Carrier for Measuring Cytoplasmic Dehydrogenatng Enzyme Activities", Histochemie, vol. 35, (1973), pp. 75–80.

Chayen et al., "Practical Histochemistry", John Wiley & Sons, New York, pp. 192–193 (1973).

Moore, M., "The Antihemorrhagic Activity of Sulfonated Derivatives of 2–Methylnaphthalene", Aug. 1941, pp. 2049–2051.

Chayen et al., "Metablism of Rheumatoid and Non–Rheumatoid Synovial Lining Cells", Articular Synovium. Int. Symp., Bruges 1981, pp. 59–74.

Paladin, Doklady Akad. Nank –USSR, vol. 41, pp. 258–261 (1943).

Primary Examiner—C. Warren Ivy
Assistant Examiner—Lyman H. Smith
Attorney, Agent, or Firm—Oliff & Berridge, PLC

[57] ABSTRACT

A redox, hydrogen-acceptor compound, having utility in treating inflammation, is a 1,4-dioxonaphthalene or 1,4-dilminon aphthalene having either a 2,3-double bond, in which cast there are 2 and 3-substituents, or a 2,3-single bond. Examples of such compounds are menadione epoxide and water-soluble derivatives or menadione such as menadione bisulphite.

16 Claims, No Drawings

NAPHTHOQUINONE DERIVATIVES FOR THE TREATMENT OF CHRONIC INFLAMMATION

This application is a 35 USC 371 filing of PCT/GB92/00196, published as WO/92/01353 on Aug. 20, 1992.

FIELD OF THE INVENTION

This invention relates to naphthoquinone derivatives, many of which are known, for which a new therapeutic utility has been found.

BACKGROUND OF THE INVENTION

Many 1,4-naphthoquinones are known. One example is menadione, or vitamin $K_3$.

Menadione (2-methyl-1,4-naphthoquinone) is a redox, hydrogen-acceptor compound that has the property of a prothrombogenic vitamin. The potential value of redox drugs, including menadione, is described by Chayen (1982), Agents and Actions 12(4): 530–535.

Rheumatoid arthritis involves a considerable increase in the activity of the oxidative section of the pentose-phosphate pathway of the synovial lining cells that grow out to form one of the histological manifestations of the disease in the affected joint. This pathway is the main source of ribose sugars that are essential for many metabolic processes, including proliferation; of greater significance is the fact that it is also a major source of the reduced coenzyme (NADPH) that is essential for many aspects of cellular activity, as reviewed by Chayen and Bitensky (1982), "Metabolism of the Rheumatoid and Non-Rheumatoid Synovial Lining", in Articular Synovium, ed. Franchimont, pub, Karger, Basle. This NADPH is provided by the activities of the first and the third component of the pathway, namely glucose 6-phosphate dehydrogenase (G6PD) and 6-phosphogluconate dehydrogenase (6PGD). The second component of the pathway is 6-phosphogluconolactonase (6PGL).

Pitsillides et al (1990), Cell Biochem. Funct. 8, 221–226, show that menadione significantly ameliorates the immune arthritis that can be induced experimentally in the rabbit (which closely resembles human rheumatoid arthritis both structurally and metabolically). By contrast with control animals, rabbits fed with menadione (by gavage) exhibited marked diminution in the chronic inflammation assessed both histologically and by the activity of which is characteristically increased in the sync lining cells in both the human and the rabbit condition Chayen et al (1973), Practical Biochemistry, Wiley, disclose that, in many cytochemical reactions, on sections of various tissues, menadione is as effective as phenazine methosulphate in transferring redu equivalents from the reduced coenzyme to the indicated neotetrazolium chloride. However, it apparently does act in this way in synovial lining cells in section human and rabbit synovium. Its mechanism of action therefore cannot be readily understood.

SUMMARY OF THE INVENTION

Naphthoquinone derivatives have been found to therapeutic utility or activity superior to menadione. present invention is in part based on the realisation that in synovial linings, menadione might be converted to epoxide, but would not be rapidly metabolised further Consequently, the unusual effect of menadione would be to the epoxide.

The present invention is also based on the realisation that menadione has a reactive site at C-3 which may make an unsuitable for oral administration, e.g. owing interaction with glutathione (reduced form). In accordance with the present invention, compounds; which have desired activity, i.e. of the same order as, or preferably better than, menadione, with respect to chronic arthritis inflammation, are better adapted to oral administration having either a 2,3-double bond, in which case there a and 3-substituents, or a 2,3-single bond.

DESCRIPTION OF THE INVENTION

One type of compound for use in the present invention is a 1,4-naphthalenedione (or imine analogue) which has a reactive site, by being substituted at the 2 and positions, e.g. of formula I. Specific examples compounds of this type are 2,3-dimethyl-1,4-naphthalenedione and 2,3-dimethoxy-1,4-naphthalenedione.

An alternative type of compound for use in the present invention is a 1,2,3,4-tetrahydro-1,4-dioxonaphthalene (or imine analogue). Depending on their substitution, such compounds can exist in a tautomeric form that is more readily apparent as aromatic, and which may be named as 1,4-naphthalene-diol. Compounds of this type are 2,3-epoxy-1,2,3,4-tetrahydro-1,4-dioxonaphthalenes, e.g. of formula II, and compounds of formula III. Specific examples of these types of compounds are menadione epoxide and menadione bisulphite, respectively.

In formulae I, II and III, each X is O or $NR^1$, $R^1$ being H or a substituent; R represents H or one or more substituents; $R^2$ and $R^3$ are each a substituent; and $R^{2a}$, $R^{2b}$ and $R^{3a}$ and $R^{3b}$ are each H or a substituent. As in the case of menadione bisulphite, wherein $R^{2a}$ and $R^{2b}$ are both substituents, aromatisation of the quinone ring is prevented.

The compounds of the inventions are preferably naphthoquinones/naphthalenediones, i.e. in which X is O. The nature of any substituents is not critical, provided that they are reasonably stable and do not substantially affect the activity of the compound, and for this reason any substituent is usually of no more than 8 C atoms, and preferably no more than 4 or, most preferably, 2 C atoms. For example, R, $R^1$ (if present), $R^2$, $R^{2a}$, $R^{2b}$, $R^3$, $R^{3a}$ and $R^{3b}$ may each be selected from $C_{1-4}$ alkyl, $C_{1-4}$ alkoxy, OH or halogen, or constitute part of a ring compound of, e.g. 5, 6 or 7 C/hetero-atoms (such as O, S or NH).

Many compounds of the given formulae are known, e.g. phthiocol, menadione epoxide, menadione sodium bisulphite, 2,3-dimethyl-1,4-naphthoquinone and 2,3-dimethoxy-1,4-naphthoquinone. Novel compounds of formula I can be prepared by means analogous to those that have previously been used to prepare the known compounds.

Some novel compounds of formula III are given here as formulae A, B, C, D, E, F and G. For the reasons given in Example 1, below, the lactones of formulae A to E a designed as inhibitors of 6PGL. Phthiocol β-glucofuranosiduronic lactone (formula D) is designed give a very stable lactone, comparable with the oxides 2,3-dimethyl-1,4-naphthoquinone and 2,3-dimethoxy-1, naphthoquinone. Furanosiduronic lactones are very stable to alkaline hydrolysis; the glycosidic linkage is likely be more labile.

The other 5- and 6-membered lactones, of formulae B, C and E, will offer varying degrees of resistance hydrolysis, due to steric effects. The lactone of formula B is likely to be the most stable of these compounds.

As has been indicated above, in addition substitution of the quinone ring, the benzene ring may also be substituted.

While 5-hydroxy substitution is not preferred, the compounds of formulae F and G exemplify such substitution.

Menadione reacts readily in aqueous solution with sodium bisulphite to form 2-methyl-1,4-dioxotetralin-sulphonate. This and other suitable water-soluble for have the following properties that are advantageous compared with menadione:

1. They are water-soluble, while menadione is lipid soluble.
2. They are loss toxic than menadione; see Pallad (143) Doklady Akad. Nank. SSSR 41, 258–261.
3. They do not have the irritancy of the fr menadione; see Moore (1941) J.A.C.S. 63, 2049
4. They are chemically stable at neutral or acid pH.
5. They have better therapeutic efficacy than menadione by virtue of their structures, red potential and solubility.
6. There is no double bond between positions 2 and 3 in the bisulphite, making it unreactive thiols which, otherwise would decrease the therapeutic effect of these compounds.
7. Menadione bisulphite has a higher redox potential than menadione.

The therapeutic efficacy of menadione bisulphite has been demonstrated by intra-articular injections in chronic RA patients. Other soluble compounds of the invention are menadiol diphosphate, menadiol disulphate and 2-methyl-1,4-naphthohydroquinone bis(hydrogen succinate), sodium salt.

Compounds for use in the invention may exist in free or complexed form. An example of a suitable complex is menadione bisulphite with vitamin $B_1$ or $B_6$, i.e. pyridoxine. An equimolar complex of the bisulphite with pyridoxine is a potentially valuable material having good stability.

The mode of action of compounds for use in accordance with this invention is believed to be generally the same as menadione, i.e. on account of their redox, hydrogen-accepting nature; see Chayen (1982), supra. Either naturally, or after solution or after metabolic change in the human body, they have a redox potential ($E_{1/8}$) more negative than −220 mV (as recorded against a standard calomel electrode, for example when dissolved in 90% ethanol—0.005M acetate buffer of pH 4.0, giving a final apparent pH of pH 6.3±0.7).

In general, the efficacy of naphthoquinones is related to their redox potential ($E_{1/8}$). Menadione ($E_{1/8}$ −220 mV) is effective (Pitsillides) et al, 1990). As described below, menadione epoxide ($E_{1/8}$ −915 mV) is very effective at half the dosage. The $E_{1/8}$ of menadione sodium bisulphite, measured in human plasma, is −640 mV. Some other $E_{1/8}$ values are given below, in Table 2.

Compounds defined herein may be formulated into any desired pharmaceutical compositions, e.g. tablets or soft gelatin capsules, with suitable excipients etc. Water-soluble forms of such compounds, such as menadione sodium bisulphite, may be formulated accordingly. The complex described above may be particularly suitable for oral administration.

The following Examples further illustrate the invention.

EXAMPLE 1

Utility of Menadione Epoxide

Twenty-two female New Zealand white rabbits (initial weight 1.5–2.0 kg) were immunised subcutaneously between the scapulae, with 0.5 ml of complete Freund's adjuvant containing 2.5 mg of ovalbumin (Sigma). A booster inoculation was given two weeks later. Four weeks after this, the right knee was challenged with an intra-articular injection (0.5 ml) of sterile saline containing ovalbumin (10 mg/ml). One week before this; twice a week for the next two weeks; and weekly thereafter, the temperature of both knees was measured on the medial side of the patella by means of a Digi-Sense thermocouple thermometer (Cole-Palmer Instrument Co., Chicago, Ill., U.S.A.). They were skin-tested before challenge to ensure that the cell-mediated immunity was equivalent in the treated and control rabbits. From six to nine weeks after challenge, twelve were treated bi-weekly with 4 ml of a solution of menadione epoxide (25 mg/kg body weight) in olive oil (Sigma) given by gavage; the other ten were given olive oil by the same route. They were killed in pairs, treated and untreated, by intravenous injection of phenobarbitone sodium at various intervals from five to nine weeks later. After removal, the synovial tissue was cut into pieces of not greater than 0.5 $cm^3$; these were immersed for up to 1 min in a 5% solution of polyvinyl alcohol containing 5% $CaCl_2.2H_2O$ (Chayen et al, 1973) and then chilled to −70° C. in n-hexane (BDH: low in aromatic hydrocarbons grade). The tissue was stored in dry tubes at −70° C. and examined within two weeks.

Sections were cut (10 μm) in a Bright's cryostat (cabinet temperature of −30° C.) with the knife cooled with solid carbon dioxide. The sections were flash-dried on to slides taken from the ambient temperature of the laboratory (Chayen et al, 1973) and stored briefly in a desiccator before being tested for enzymatic activity.

Depending on the amount of tissue, sections were taken from up to fifteen regions of each challenged joint and stained with 0.1% toluidine blue in 0.1M acetate buffer, pH 6.1. They were assessed for thickening of the synovial lining cell layer; degree of infiltration by both chronic and acute inflammatory cells; and fibrosis. Each of these criteria was evaluated on a scale that ranged from 0 to ++. A value based on all these criteria was given for the response in each challenged joint and the degree of inflammation of the whole joint was assessed on an arbitrary scale of − to ++.

Results:

The overall difference in temperature between challenged and unchallenged knees, in a control rabbit and a treated rabbit, expressed per day, during the period commencing two weeks after the start of treatment until the animals were killed, was 0.7110° C. in the control rabbit, as against 0.096° C. in the menadione epoxide-treated rabbit.

The median value for the overall difference in temperature expressed per day, in the group of rabbits treated with menadione epoxide, during the period commencing two weeks after treatment until the animals were killed, was 0.096° C. day (interquartile range 0.008 to 0.345° C./day). In the control group, the median value obtained was 0.589°C./day with an interquartile range of 0.308 to 0.687°C./day (p=0.04).

The overall assessment of the degree of inflammation in the challenged joint of the ten untreated rabbits was as follows: one rabbit was evaluated as ++, six were +, one was ±, and two were not inflamed. Of the twelve treated with menadione epoxide, one was evaluated +, four as ±, six as ±, and one totally negative (−).

In summary, treating the established chronic inflammation by the oral administration of menadione epoxide caused a marked decrease in the inflammation as assessed by measurement of temperature in vivo, by visual inspection post mortem, and by histological examination.

As indicated above, available evidence suggests that the prime factor involved in rheumatoid arthritis may be elevated G6PD activity. Generally, when the G6PD activity is elevated, that of 6PGL is elevated equivalently. The main effect of menadione epoxide was to decrease both activities towards normal levels. It was therefore difficult to determine which was affected by the menadione epoxide. However, there was a secondary effect, found in the activities in the desquamating cells. In these, the G6PD activity was very elevated: e.g. 45.7 units as against 25.5 units in the "rheumatoid" synovial lining cells of the intact lining, and 6 units in synovial lining cells of normal joints. Despite this, there was no equivalent increase in the 6PGL activity, indicating that the effect of the menadione epoxide was predominantly on the lactonase activity. It may therefore be appropriate to measure both activities, as an indication of therapeutic utility.

EXAMPLE 2

Utility of 2,3-(Dimethoxy or dimethyl)-1,4-naphthoquinone

In each of separate groups of six, rabbits were treated with the same volume of either olive oil alone or dimethoxynaphthoquinone in olive oil for six weeks after the initiation of arthritis (six weeks after challenge). The treatment was 25 mg/kg orally twice a week.

The rabbits were investigated for the concentration of G6PD, 6PGL and 6PGD in synovial lining cells. The respective mean values (±SEM) for the treatment of olive oil alone were 15.4±1.9, 2.5±0.3 and 8.2±1.1; the results for those treated with dimethoxynaphthoquinone were 7.7±1.2, negligible and 4.6±1.1. All three enzyme activities were thus greatly reduced.

Comparative experiments with 8 individual rabbits, in which arthritis was induced for 6 weeks, were also conducted. The treatment was with olive oil alone or a naphthoquinone (50 mg/kg) for 4 weeks, or for 4 weeks followed by a further 4 weeks with no treatment. The G6PD activities that were found in the joints are tabulated below.

EXAMPLE 3

Utility of Menadione Bisulphite

Two human patients suffering from chronic arthritic inflammation were given intra-articular injections of menadione bisulphite. The G6PD activity (mean integrated extinction $\times 10^3/10$ min) and lysosomal latency (% bound activity) were measured before and after injection. The G6PD activity decreased from 423 to 188 in one case and from 245 to 127 in the other; the lysosomal latency increased, respectively from 0 to 13 and from 0 to 31 (normal values are around 40% latency).

EXAMPLE 4

Comparative Menadione Derivatives

The percentage decreases in G5PD activity (mean±SEM) in the synovial lining cells of human rheumatoid tissue maintained in vitro, induced by naphthoquinone of formula I (R=H, X=O), including compounds outside the scope of the invention, are given in Table 2.

TABLE 2

| Compound | $E_{1/2}$ (mV) | % decrease in G6PD |
| --- | --- | --- |
| menadione | −220 | 38 ± 6.9 |
| 3-glutathionylmenadione | −170 | 37 ± 13.0 |
| 3-homocysteinylmenadione | −190 | 25 ± 9.7 |
| phthiocol | −355 | 47 ± 11.5 |
| dimethoxynaphthoquinone | −250 | 49 ± 14.0 |
| dimethylnaphthoquinone | −290 | 61 |

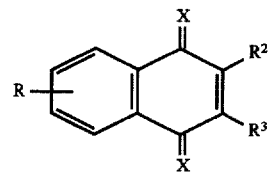

I

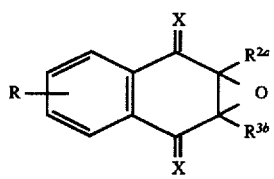

II

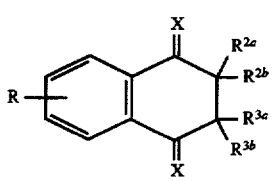

III

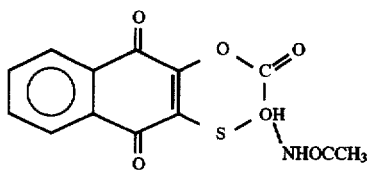

'A'

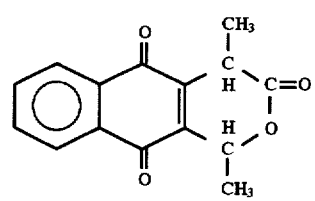

'B'

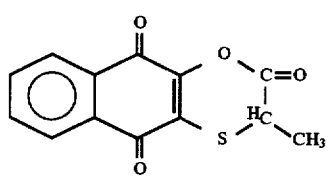

'C'

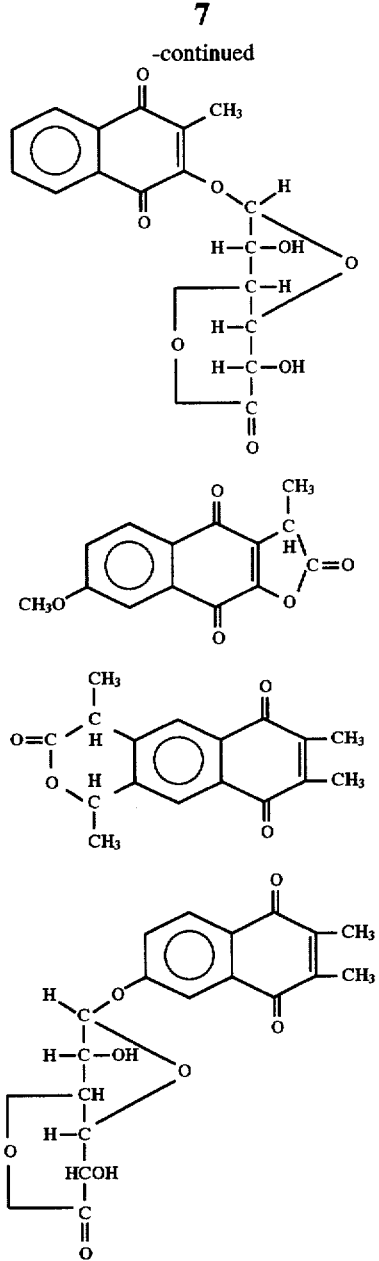

We claim:

1. A method of treating chronic inflammation, comprising administering to a human subject a composition comprising a compound having a redox potential that is more electronegative than that of menadione, wherein said compound is selected from the group consisting of 1,4-dioxonaphthalenes, 1-oxo-4-iminonaphthalenes, 1-imino-4-oxonaphthalenes and 1,4-diiminonaphthalenes, and wherein said compound has a $C_2$-$C_3$ single bond.

2. The method according to claim 1, wherein the compound is selected from:

2,3-disubstituted-1,4-naphthalenediones, 2,3-epoxy-1,2,3,4-tetrahydro-1,4-dioxonaphthalenes, and analogues thereof wherein at least one oxo group is replaced by $NR^1$, $R^1$ being H or a substituent.

3. The method according to claim 1, wherein the inflammation is chronic arthritic inflammation.

4. The method according to claim 1, wherein the compound is a menadione derivative.

5. The method according to claim 1, wherein the compound is a menadione bisulphite.

6. The method according to claim 1, wherein said composition is administered in an inflammation-relieving amount.

7. A method according to claim 1 wherein said group consists of 1,4-dioxonapthalenes.

8. A method according to claim 1 wherein said group consists of 1,4-diiminonapthalenes.

9. A method according to claim 5, wherein said composition is administered orally.

10. A method according to claim 9, wherein said composition is administered in at least one form selected from the group consisting of a tablet and a gelatin capsule.

11. A method according to claim 9, wherein said composition is administered in an oil.

12. A method according to claim 1, wherein said composition is administered orally.

13. A method according to claim 12, wherein said composition is administered in at least one form selected from the group consisting of a tablet and a gelatin capsule.

14. A method according to claim 12, wherein said composition is administered in an oil.

15. A method of treating chronic inflammation, comprising administering to a human subject exhibiting chronic rheumatoid arthritic inflammation a composition comprising a compound having a redox potential that is more electronegative than that of menadione, wherein said compound is selected from the group consisting of 1,4-dioxonaphthalenes, 1-oxo-4-iminonaphthalenes, 1-imino-4-oxonaphthalenes and 1,4-diiminonaphthalenes, and wherein said compound has a $C_2$-$C_3$ single bond.

16. The method according to claim 15, wherein said compound is menadione bisulphite.

* * * * *